United States Patent
Piehl

(10) Patent No.: US 7,621,942 B2
(45) Date of Patent: Nov. 24, 2009

(54) VARIABLE GEOMETRY OCCIPITAL FIXATION PLATE

(75) Inventor: Jason Piehl, Apple Valley, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 68 days.

(21) Appl. No.: 11/085,672

(22) Filed: Mar. 21, 2005

(65) Prior Publication Data
US 2006/0229610 A1 Oct. 12, 2006

(51) Int. Cl.
*A61B 17/88* (2006.01)

(52) U.S. Cl. .................. 606/281; 606/71; 606/279; 606/283; 606/280

(58) Field of Classification Search ............ 606/69–71, 606/250, 251, 252, 253, 254, 255, 256, 257, 606/258, 259, 260, 280, 70, 281, 282, 283, 606/284, 285, 286, 287, 288, 289, 290, 291, 606/292, 293, 294, 295, 296, 297, 298, 299, 606/246, 249, 279; 623/17.11
See application file for complete search history.

(56) References Cited

U.S. PATENT DOCUMENTS

| | | | |
|---|---|---|---|
| 4,763,644 A | 8/1988 | Webb | |
| 4,805,602 A | 2/1989 | Puno | |
| 4,836,193 A | 6/1989 | Ransford | |
| 4,841,959 A | 6/1989 | Ransford | |
| 4,887,596 A | 12/1989 | Sherman | |
| 4,950,269 A | 8/1990 | Gaines, Jr. | |
| 5,129,388 A | 7/1992 | Vignaud | |
| 5,360,429 A | 11/1994 | Jeanson et al. | |
| 5,498,264 A | 3/1996 | Schlapfer et al. | |
| 5,507,745 A | 4/1996 | Logroscino et al. | |
| 5,520,689 A | 5/1996 | Schlapfer et al. | |
| 5,531,745 A * | 7/1996 | Ray .......................... 606/261 | |
| 5,542,946 A | 8/1996 | Logroscino et al. | |
| 5,545,164 A | 8/1996 | Howland | |
| 5,558,674 A | 9/1996 | Heggeness et al. | |
| 5,653,708 A | 8/1997 | Howland et al. | |

(Continued)

FOREIGN PATENT DOCUMENTS

EP 0 737 449 A1 10/1996

(Continued)

OTHER PUBLICATIONS

International Search Report mailed on Jul. 19, 2007 for International Application No. PCT/US2006/009996.
Written Opinion mailed on Jul. 19, 2007 for International Application No. PCT/US2006/009996.

(Continued)

*Primary Examiner*—Eduardo C Robert
*Assistant Examiner*—Jan Christopher Merene
(74) *Attorney, Agent, or Firm*—Sprinkle IP Law Group

(57) ABSTRACT

A fixation device for connecting a stabilization device to a bone comprises a first member comprising a first portion for attachment to a bone; a second member comprising a second portion for attachment to a bone and connected to the first member by a pivotal connection such that the first and second portions are spaced apart by an adjustable distance, at least one of the first and second members further comprising a portion for mounting a connector adapted to secure a stabilization device.

7 Claims, 6 Drawing Sheets

U.S. PATENT DOCUMENTS

| | | | |
|---|---|---|---|
| 5,707,372 A * | 1/1998 | Errico et al. | 606/61 |
| 5,713,898 A | 2/1998 | Stucker et al. | |
| 5,928,233 A * | 7/1999 | Apfelbaum et al. | 606/261 |
| 5,976,135 A | 11/1999 | Sherman et al. | |
| 6,017,343 A * | 1/2000 | Rogozinski | 606/61 |
| 6,077,262 A | 6/2000 | Schlapfer et al. | |
| 6,146,382 A | 11/2000 | Hurlbert | |
| 6,187,005 B1 | 2/2001 | Brace et al. | |
| 6,238,396 B1 * | 5/2001 | Lombardo | 606/61 |
| 6,296,644 B1 | 10/2001 | Saurat et al. | |
| 6,302,883 B1 | 10/2001 | Bono | |
| 6,315,779 B1 | 11/2001 | Morrison | |
| 6,336,927 B2 * | 1/2002 | Rogozinski | 606/286 |
| 6,368,351 B1 * | 4/2002 | Glenn et al. | 623/17.15 |
| 6,379,358 B1 | 4/2002 | Kuo | |
| 6,432,109 B1 | 8/2002 | Letendart et al. | |
| 6,485,491 B1 | 11/2002 | Farris et al. | |
| 6,524,315 B1 | 2/2003 | Selvitelli et al. | |
| 6,547,790 B2 | 4/2003 | Harkey, III et al. | |
| 6,620,164 B2 | 9/2003 | Ueyama et al. | |
| 6,682,532 B2 | 1/2004 | Johnson | |
| 6,832,999 B2 | 12/2004 | Ueyama et al. | |
| 6,902,565 B2 | 6/2005 | Berger et al. | |
| 6,949,123 B2 * | 9/2005 | Reiley | 623/17.11 |
| 6,958,065 B2 | 10/2005 | Ueyama et al. | |
| 7,033,377 B2 | 4/2006 | Miller | |
| 7,060,069 B2 | 6/2006 | Kozak et al. | |
| 7,232,441 B2 | 6/2007 | Altarac et al. | |
| 7,250,052 B2 | 7/2007 | Landry et al. | |
| 7,491,218 B2 | 2/2009 | Landry et al. | |
| 2002/0049446 A1 * | 4/2002 | Harkey et al. | 606/70 |
| 2002/0120268 A1 | 8/2002 | Berger | |
| 2003/0004512 A1 | 1/2003 | Farris et al. | |
| 2003/0036759 A1 | 2/2003 | Musso | |
| 2003/0153913 A1 | 8/2003 | Altarac et al. | |
| 2003/0163132 A1 * | 8/2003 | Chin | 606/61 |
| 2003/0176863 A1 | 9/2003 | Ueyama et al. | |
| 2004/0122426 A1 | 6/2004 | Michelson | |
| 2004/0127904 A1 | 7/2004 | Konieczynski et al. | |
| 2004/0153070 A1 | 8/2004 | Barker et al. | |
| 2004/0172022 A1 | 9/2004 | Landry | |
| 2004/0267259 A1 | 12/2004 | Mazda et al. | |
| 2005/0010227 A1 | 1/2005 | Paul | |
| 2005/0080417 A1 | 4/2005 | Alexis et al. | |
| 2005/0124994 A1 | 6/2005 | Berger et al. | |
| 2005/0216005 A1 * | 9/2005 | Howland | 606/61 |
| 2005/0228382 A1 | 10/2005 | Richelsoph et al. | |
| 2005/0240185 A1 * | 10/2005 | Boomer et al. | 606/69 |
| 2005/0251141 A1 | 11/2005 | Frigg et al. | |
| 2005/0273104 A1 | 12/2005 | Oepen et al. | |
| 2005/0277939 A1 | 12/2005 | Miller | |
| 2005/0283153 A1 | 12/2005 | Poyner et al. | |
| 2005/0288669 A1 | 12/2005 | Abdou | |
| 2006/0004359 A1 | 1/2006 | Kramer et al. | |
| 2006/0004360 A1 | 1/2006 | Kramer et al. | |
| 2006/0004363 A1 | 1/2006 | Brockmeyer et al. | |
| 2006/0155284 A1 | 7/2006 | Doherty et al. | |
| 2006/0184170 A1 | 8/2006 | Kapitan et al. | |
| 2006/0217710 A1 | 9/2006 | Abdou | |
| 2006/0217723 A1 * | 9/2006 | Suh | 606/71 |
| 2006/0264932 A1 | 11/2006 | Bert | |
| 2007/0016189 A1 | 1/2007 | Lake | |
| 2007/0083201 A1 | 4/2007 | Jones et al. | |
| 2007/0118121 A1 | 5/2007 | Purcell et al. | |
| 2007/0123872 A1 | 5/2007 | Brockmeyer et al. | |
| 2007/0299441 A1 | 12/2007 | Hoffman | |
| 2008/0051783 A1 | 2/2008 | Null et al. | |
| 2008/0086124 A1 | 4/2008 | Forton | |
| 2008/0125781 A1 | 5/2008 | Hoffman | |
| 2008/0147123 A1 | 6/2008 | Schermerhorn | |
| 2008/0177313 A1 | 7/2008 | Lemoine | |
| 2008/0177314 A1 | 7/2008 | Lemoine | |
| 2008/0300635 A1 * | 12/2008 | Lieponis | 606/280 |

FOREIGN PATENT DOCUMENTS

| | | |
|---|---|---|
| EP | 1180348 B1 | 12/2008 |
| FR | 2 687 567 A1 | 2/1992 |
| FR | 2 760 629 A1 | 3/1997 |
| WO | WO 95/31147 | 11/1995 |
| WO | WO 97/23170 | 7/1997 |
| WO | WO 98/41160 | 9/1998 |
| WO | WO 2005122922 A2 | 12/2005 |
| WO | WO 2006019370 A1 | 2/2006 |
| WO | WO2006/102222 A2 | 9/2006 |
| WO | WO 2006096756 A2 | 9/2006 |
| WO | WO 2007044716 A1 | 4/2007 |
| WO | WO2006/102222 A3 | 9/2007 |
| WO | WO 2007146482 A2 | 12/2007 |
| WO | WO 2008042633 A2 | 4/2008 |

OTHER PUBLICATIONS

International Preliminary Report on Patentability mailed on Sep. 25, 2007 for International Application No. PCT/US2006/009996.

Interpore Cross International, "Introducing the Altrius OCT System," Biological & Structural Innovation, Interpore Cross Intl, Irvine, CA, Copyright 2003, 2 pages.

Blackstone Medical Inc., "Ascent Posterior Occipital Cervico-Thoracic System," Cervical and Thoracolumbar Systems, www.blackstonemedical.com., Copyright 2005, 1 page.

Globus Medical, Cervical Webpage, Copyright 2005, downloaded from http://wwvv.globusmedical.com/products/cervical.php, on Feb. 2, 2006, 1 page.

Globus Medical, Protex CT . . . the new standard in OCT Stabilization systems, www.globusmedical.com, 1-866-456-2871, undated, 1 page.

Depuy Spine, "Mountaineer OCT Spinal System," Copyright 2006, DePuy Spine, Inc., Raynham, MA, Mar. 2005, 6 pages.

International Search Report and Written Opinion issued in PCT/US2007/066039, mailed Apr. 14, 2008, Zimmer Spine, Inc., 11 pages.

International Search Report and Written Opinion in PCT/US2007/079295 mailed Apr. 17, 2008, Abbott Laboratories, 14 pages.

Office Action issued in U.S. Appl. No. 11/423,201 mailed Sep. 3, 2008, Hoffman, 15 pages.

Office Action issued in U.S. Appl. No. 11/423,201 mailed Dec. 10, 2008, Hoffman, 17 pages.

International Preliminary Report on Patentability and Written Opinion issued in PCT/US2007/066039, mailed Dec. 10, 2008, Zimmer Spine, Inc., 6 pages.

Office Action issued in U.S. Appl. No. 11/423,201 mailed Mar. 5, 2009, Hoffman, 15 pages.

Office Action issued in U.S. Appl. No. 11/542,786 mailed Mar. 5, 2009, Forton, 7 pages.

Office Action issued in U.S. Appl. No. 11/563,902 mailed May 8, 2009, Hoffman, 9 pages.

International Preliminary Report on Patentability and Written Opinion issued in PCT/US2007/079295 mailed Apr. 7, 2009, Abbott Laboratories, 7 pages.

Office Action issued in U.S. Appl. No. 11/616,720 mailed May 27, 2009, Lemoine, 8 pages.

International Preliminary Report on Patentability, Chapter I, and Written Opinion issued in PCT/US2007/085190, mailed Jun. 30, 2009, Abbott Spine Inc., 8 pages.

International Search Report and Written Opinion, PCT/US2007/085190, mailed Jun. 3, 2008, 13 pages.

Office Action issued in U.S. Appl. No. 11/756,106 mailed Aug. 26, 2009, 7 pages.

Summit SI OCT Spinal Fixation System, 2 pages.

Stryker Spine Products,"Products: Cervical OASYS" Webpage, 1 page.

Blackstone Ascent, Product Information Page, 1 page.

* cited by examiner

VARIABLE GEOMETRY OCCIPITAL FIXATION PLATE

TECHNICAL FIELD

The present invention relates generally to fixation devices used in orthopedic surgery. This invention relates more particularly to devices used for cervical posterior fixation by means of a plate attached to a bone in the occipital region and secured to a rod which attaches to a cable, wire, plate, or screw fastened in the spinal region.

BACKGROUND

Fixation devices are used in orthopedic surgery to stabilize bones such as those in the spinal column. One type of fixation device includes a plate attachable to a portion of a bone. The plate may be connected to another bone or another portion of the same bone, directly or through other connecting devices. For example, posterior fixation devices can include a plate fastened to the skull, or occiput, one or more rods running longitudinally along the spine and connected to the plate, and plates, cables, wires, hooks, screws, or other connectors attached to a vertebra and connected to the rod.

A number of such mechanisms are known in the act. To accommodate the variation in patient size and anatomy, a plate often needs to be chosen from a set of plates of multiple sizes and/or varying geometry. This results in a higher cost of the device assembly and a need to maintain separate inventory of the various size and geometry devices. It also increases the surgical time because the surgeon must search for the device that best fits the patient. Accordingly, there is a need for an improved fixation plate.

SUMMARY

A fixation device for connecting a stabilization device to a bone comprises a first member comprising a first portion for attachment to a bone; a second member comprising a second portion for attachment to a bone and connected to the first member by a pivotal connection such that the first and second portions are spaced apart by an adjustable distance, at least one of the first and second members further comprising a portion for mounting a connector adapted to secure a stabilization device A method of attaching a stabilization device to a bone comprises attaching a first plate to a bone at a first portion on the first plate; attaching a second plate, pivotally attached to the first plate, to a bone at a second portion on the second plate; pivotally adjusting the position of the second plate relative to the first plate to adjust the distance between the first portion and the second portion; and attaching a stabilization device to either the first plate or the second plate.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
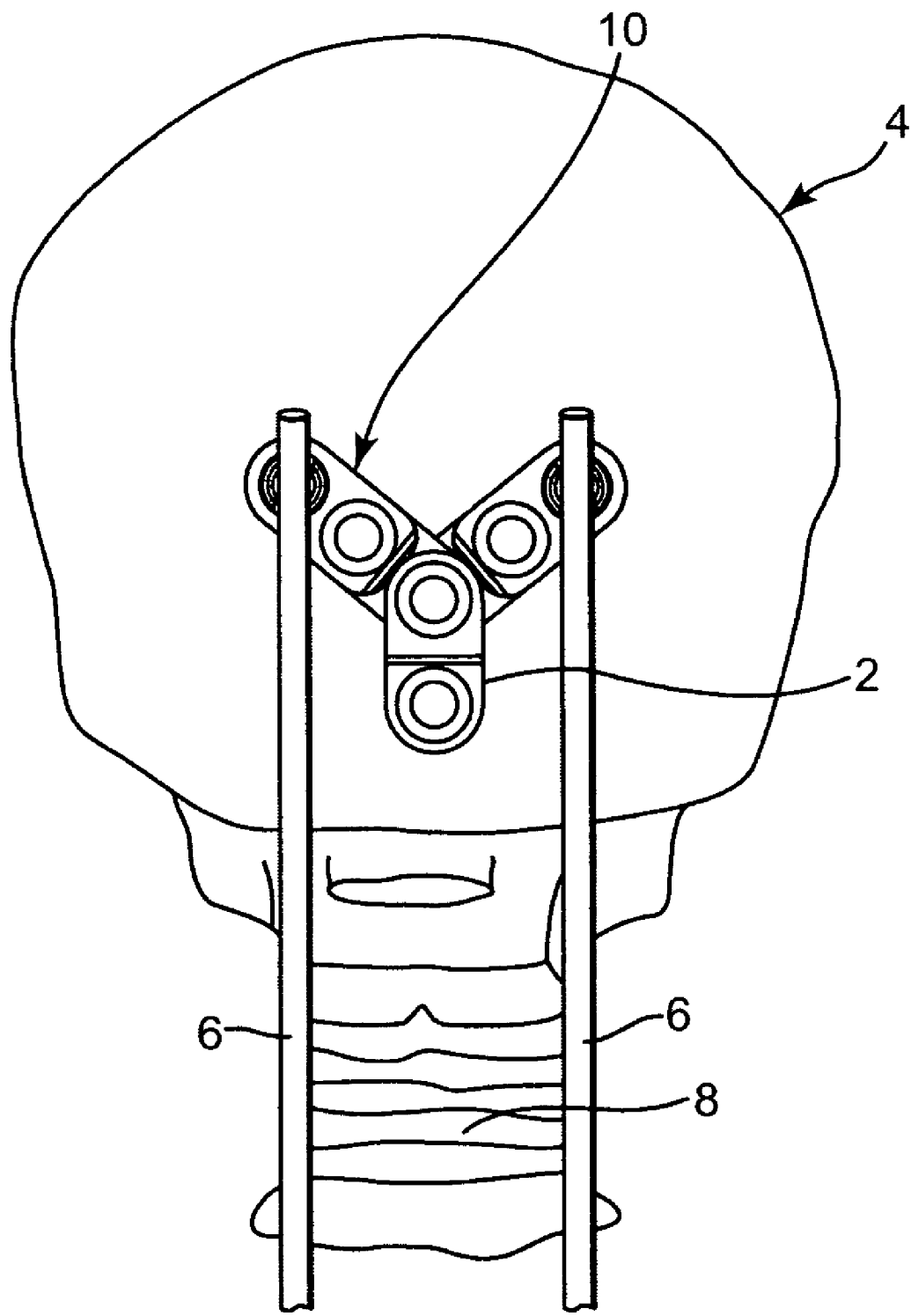
FIG. 1 shows a variable geometry occipital device, according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 shows a variable geometry occipital device 10 in one embodiment of the present invention. The variable geometry occipital device 10 in this case is affixed to the occiput 2 of the patient 4. One or more rods 6 are attached to the device 10 and run substantially along the spine column 8 and are attached to various segments of the spinal column 8.

Figure 2:
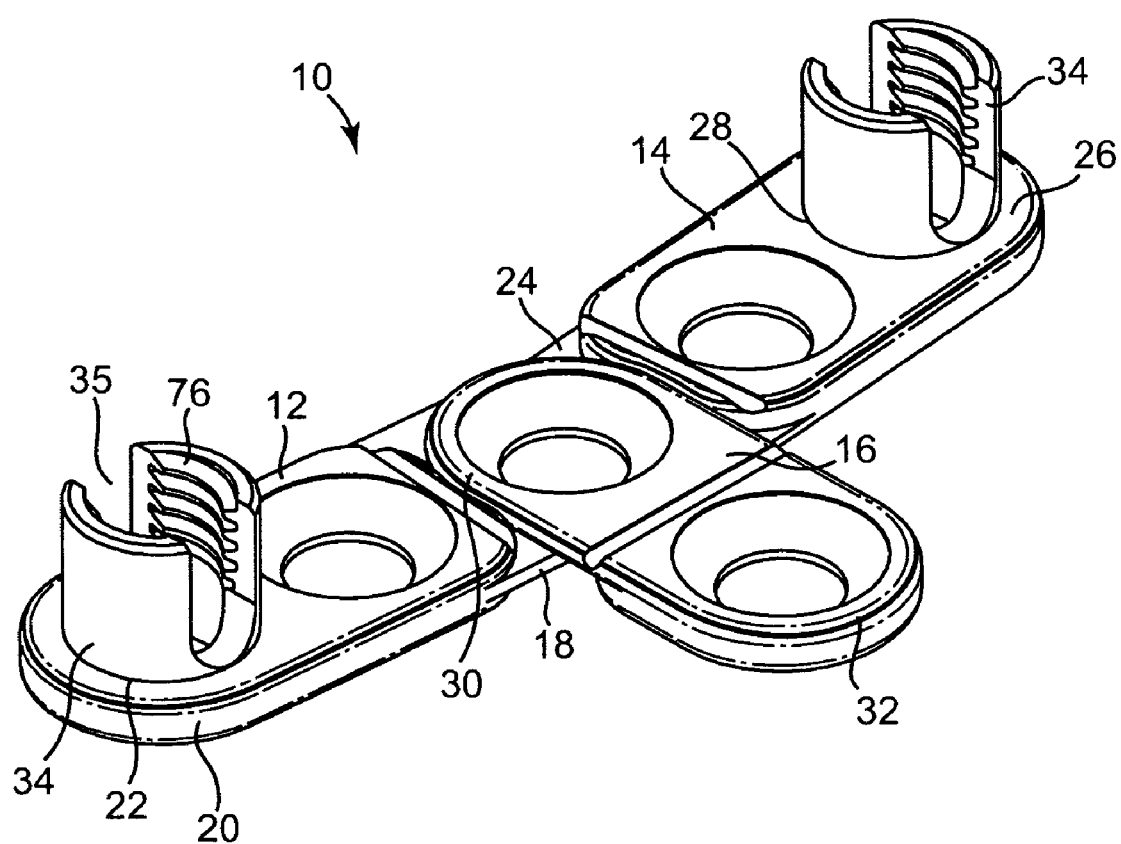
FIG. 2 shows a perspective view of the variable geometry occipital fixation device of FIG. 1

FIG. 2 shows a perspective view of the variable geometry occipital device 10 of FIG. 1. The variable geometry occipital fixation device 10 includes a first lateral member 12, a second lateral member 14, and a midline member 16. The first lateral member includes a proximal end 18, a distal end 20, and an attachment bore 22 located at the distal end 20.

The second lateral member includes a proximal end 24, a distal end 26, and an attachment bore 28 located at the distal end 26. The midline member includes a proximal end 30 and a distal end 32. In the embodiment shown in FIG. 2, the proximal ends 18, 24, and 30 are stacked on top of each other. Attachment bosses 34 are inserted into the attachment bores 22 and 28. Each attachment boss 34 has a slot 35 for receiving a stabilization device such as a rod, a cable or a cord. The attachment boss 34 further has a threaded portion 76 for receiving a threaded fastener, such as a set screw, which can be tightened directly or indirectly (e.g., through a spacer) against the stabilization device to retain it in the slot 35. Any other suitable connectors for securing stabilization devices can be used instead of the attachment bosses 34 to achieve the desired performance.

Figure 3:
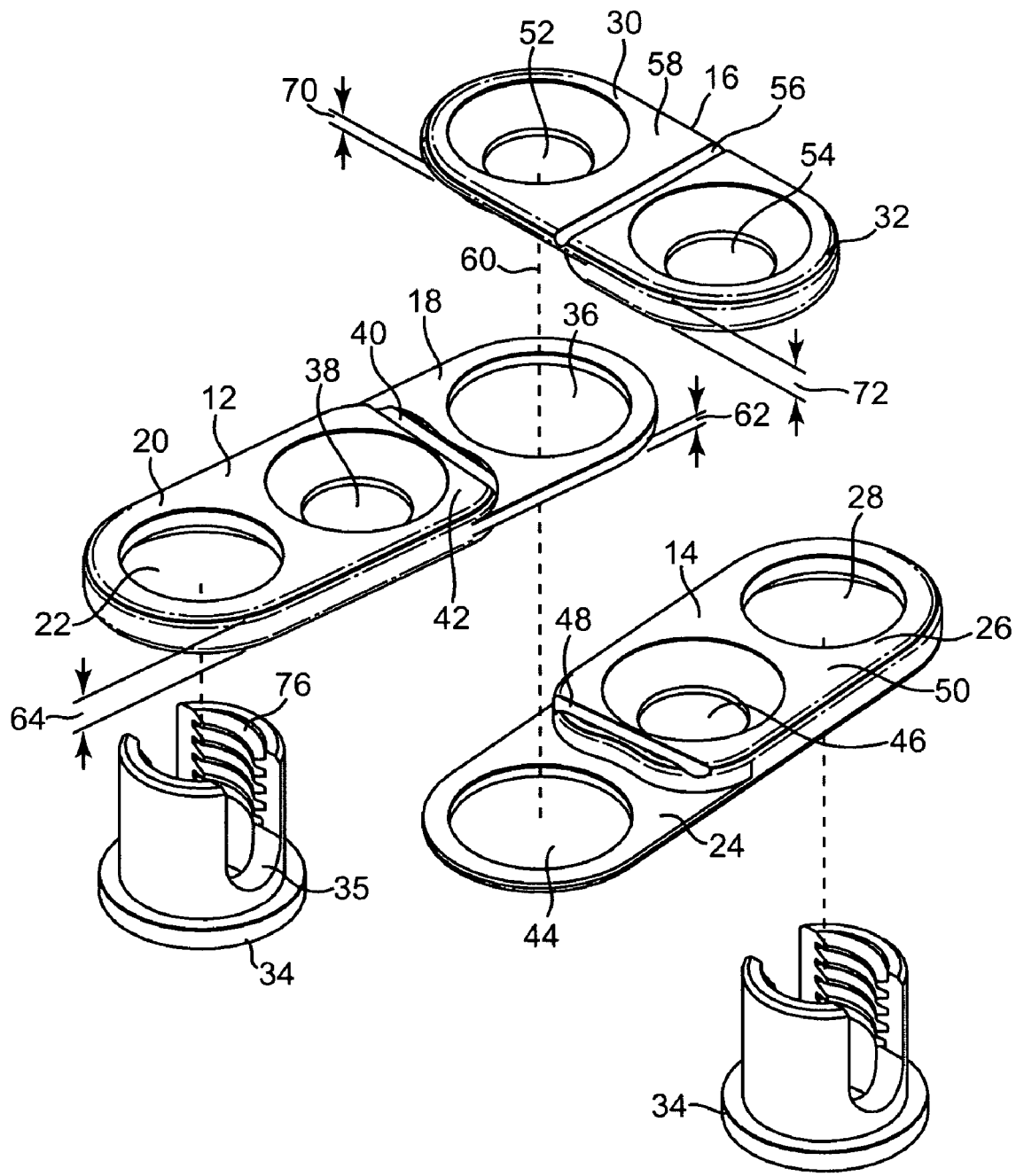
FIG. 3 shows an exploded view of the variable geometry occipital fixation device of FIG. 1.

FIG. 3 shows an exploded view of the variable geometry occipital fixation device 10 of FIG. 1. The first lateral member 12 includes the attachment bore 22, a pivot bore 36 located at the proximal end 18, and a fixation bore 38 interposed between the attachment bore 22 and the pivot bore 36. A groove 40 is interposed between the proximal end 18 and the distal end 20. The groove 40 facilitates bending of the first lateral member 12 so that it conforms to the occiput. In the embodiment shown in FIG. 3, the groove 40 is located on a top surface 42. The groove 40 could alternatively be located in any other suitable area. Alternatively, the first lateral member 12 could have more than one groove 40, or no groove at all.

Similarly, the second lateral member 14 includes a pivot bore 44 located at the proximal end 24, the attachment bore 28 located at the distal end 26, and a fixation bore 46 interposed between the attachment bore 28 and the pivot bore 44. A groove 48 is interposed between the proximal end 24 and the distal end 26 and is located on a top surface 50. Alternatively, the groove 48 could be located in some other suitable area. The second lateral member 14 could include any appropriate number of grooves 48.

The midline member 16 includes a proximal end 30 and a distal end 32. A pivot bore 52 is located at the proximal end 30 and a fixation bore 54 is located at the distal end 32. A groove 56 is interposed between the proximal end 30 and the distal end 32 and is located on a top surface 58. The midline member 16 could include any appropriate number of grooves 56 located in any suitable area.

In the embodiment shown in FIGS. 1-3, the pivot bores 36, 44, and 52 are aligned so that the first lateral member 12 and the second lateral member 14 rotate around a common axis 60. The thickness 62 of the proximal end 18 of the first lateral member 12 is less than the thickness 64 of the distal end 20. Similarly, the thickness 66 of the proximal end 24 of the second lateral member 14 is less than the thickness 68 of the distal end 26. The thickness 70 of the proximal end 30 of the midline member 16 is also less than the thickness 72 of the distal end 32. In this manner, when the three members 12, 14, and 16 are assembled together and installed in the patient 4, the thickness of the occipital device 10 is substantially uniform across the members 12, 14, and 16 and the stacked portions of members 12, 14, and 16. However, the invention is not limited to a device of such uniform thickness. The thicknesses 64, 68, and 72 need not be less than the thicknesses 66, 70, and 74 or be less by the same amounts as in this illustrative embodiment of the invention.

In the embodiment shown in FIGS. 1-3, the fixation bore 38 in the first lateral member 12 is countersunk so that when a fastener (not shown) is inserted into fixation bore 38, the height of the fastener protruding above the top surface 42 is minimized. The fixation bores 46 and 54 in the second lateral member 14 and the midline member 16 are also countersunk in a similar manner. Alternatively, some or all of the fixation bores 38, 46, and 54 need not be countersunk.

The three members 12, 14, and 16 can be attached to each other in a number of ways. In one embodiment of the invention, the members are swaged together so that they remain attached to each other while being handled but can be manipulated into different angular relationships to each other. Alternatively, the three members 12, 14, and 16 can remain separate until implantation into the patient 4, when they become linked to one another by the insertion of a fastener (not shown) into the pivot bores 36, 44, and 52. The fastener could be a rivet, screw, or any other suitable fastener.

Figure 4:
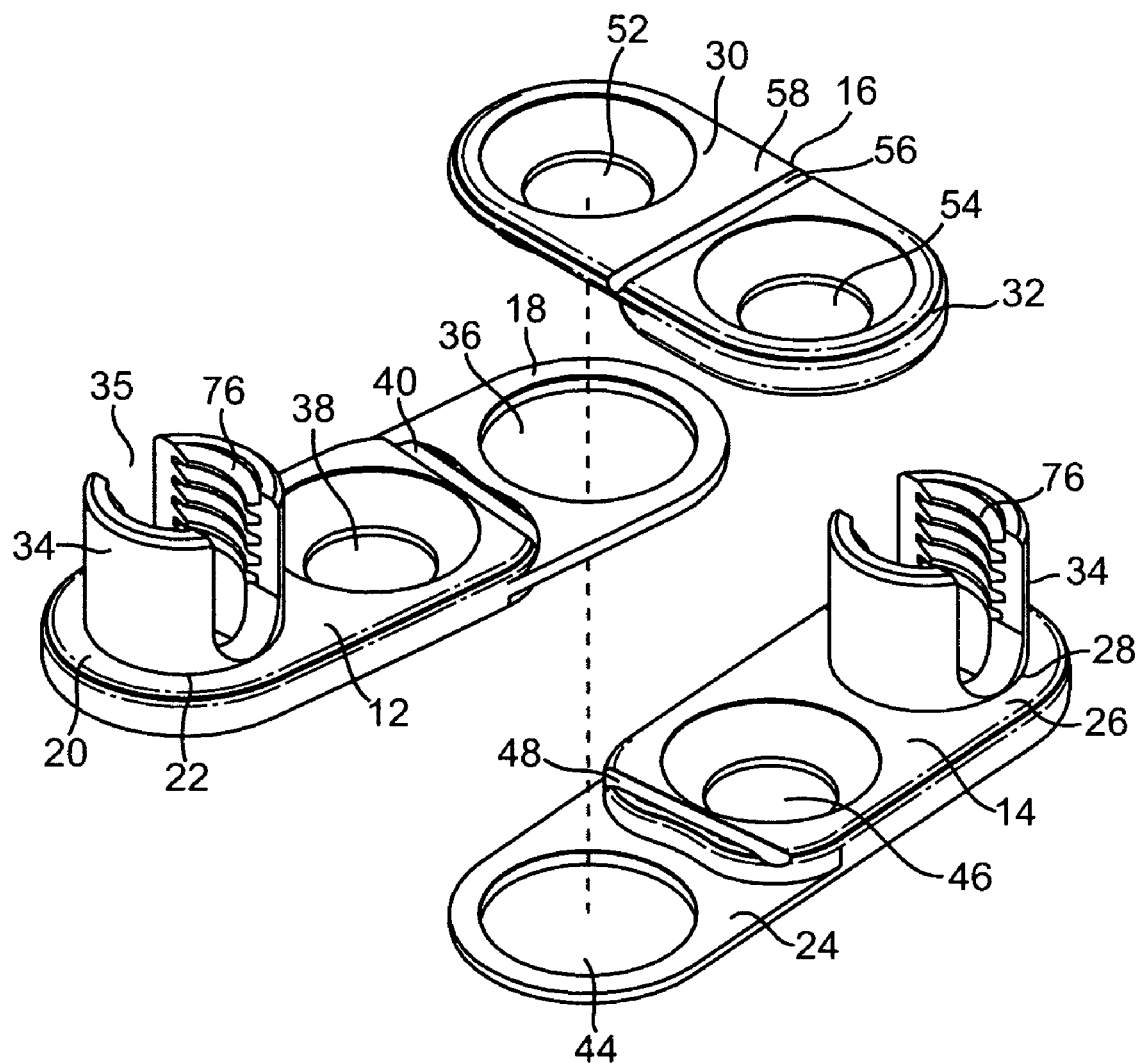
FIG. 4 shows another exploded view of the variable geometry occipital fixation device of FIG. 1 after insertion of the attachment bosses.

FIG. 4 is a perspective and partially exploded view of the variable geometry occipital fixation device 10 of FIG. 1 after insertion of the attachment bosses 34 into attachment bores 22 and 28. In the embodiment shown in FIG. 4, the attachment bosses 34 are inserted into the attachment bores 22 and 28. The attachment bosses 34 could be press-fit, riveted or swaged into the attachment bores 22 and 28 or inserted in any other suitable manner. The attachment bosses 34 preferably are free to rotate inside of the bores 22 and 28 so as to maintain the orientation of the stabilization device after the orientations of the lateral members 12 and 14 are adjusted.

Figure 5A:
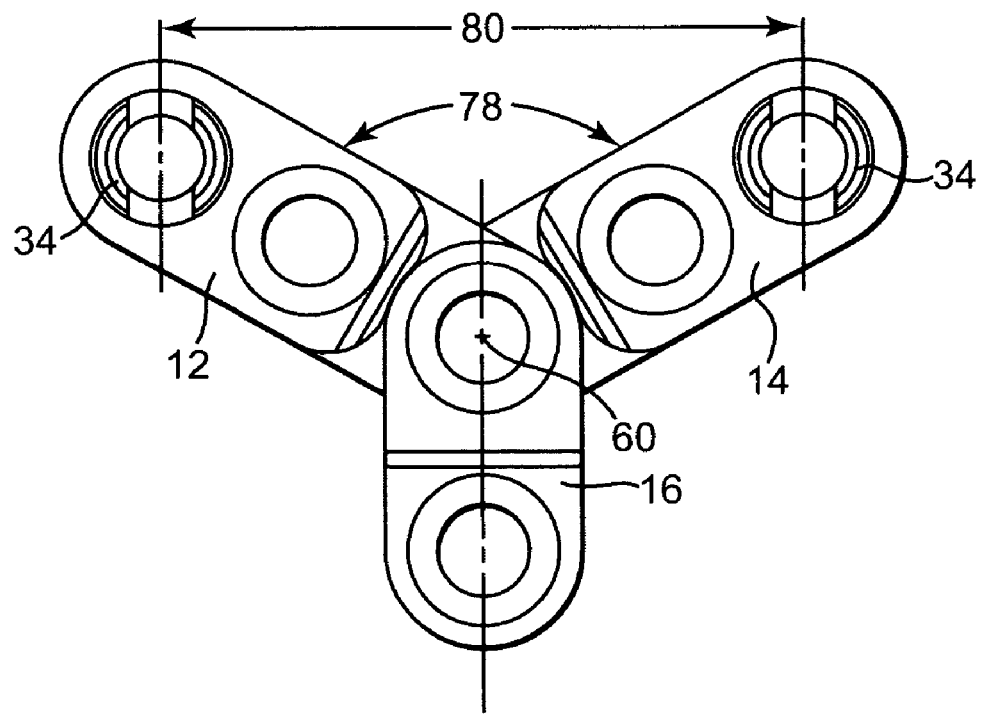
FIG. 5A shows a top plan view of the variable geometry occipital fixation device of FIG. 1 in its narrowest configuration.

FIG. 5A shows a top plan view of the variable geometry occipital fixation device 10 shown in a narrow configuration. As shown in FIG. 5A, the angle 78 between the lateral members 12 and 14 is relatively small, thereby reducing the distance 80 between the bosses 34. The angle 78 can vary as needed achieve the desired distance 80.

Figure 5B:
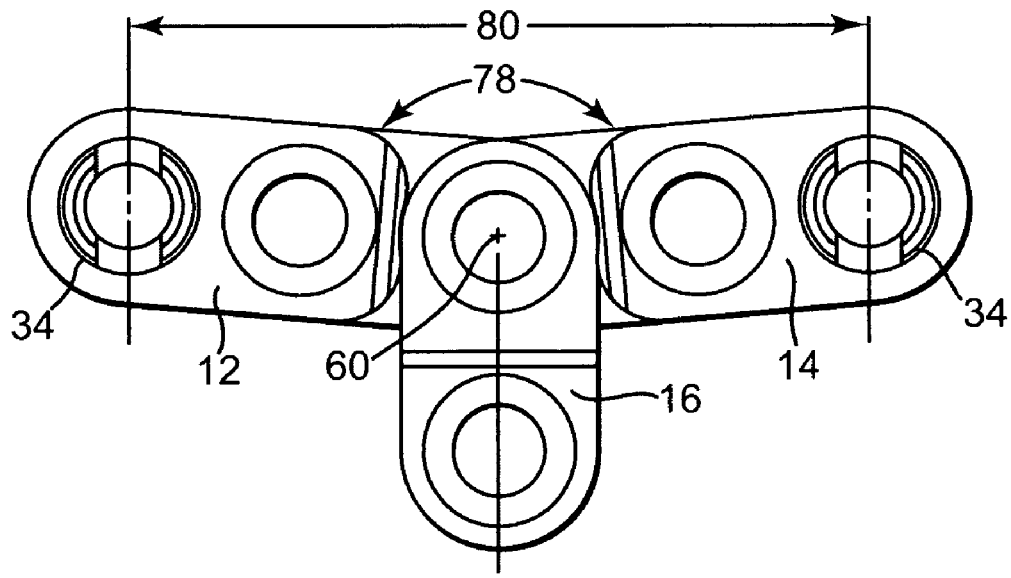
FIG. 5B shows a top plan view of the variable geometry occipital fixation device of FIG. 1 in its widest configuration.

FIG. 5B shows a top plan view of the variable geometry occipital fixation device 10 shown in a wide configuration. As shown in FIG. 5B, the angle 78 between the lateral members 12 and 14 is larger than the angle 78 shown in FIG. 5A, thereby spanning a larger distance 80 between the bosses 34 than shown in FIG. 5A. In one embodiment of the present invention, the angle 78 is approximately 100 degrees when the distance 80 is minimized and is approximately 170 degrees when the distance 80 is maximized. The available range for angle 80 need not be limited to these angles, but instead can include any desirable range.

The first and second lateral members 12 and 14 and the midline member 16 can include any configuration of fixation bores, attachment bores, and pivot bores suitable for achieving the desired variability in the distance 78 between the attachment bores 24 and 38. The number and the location of the fixation bores, attachment bores, and pivot bores can vary as needed.

Figure 6:
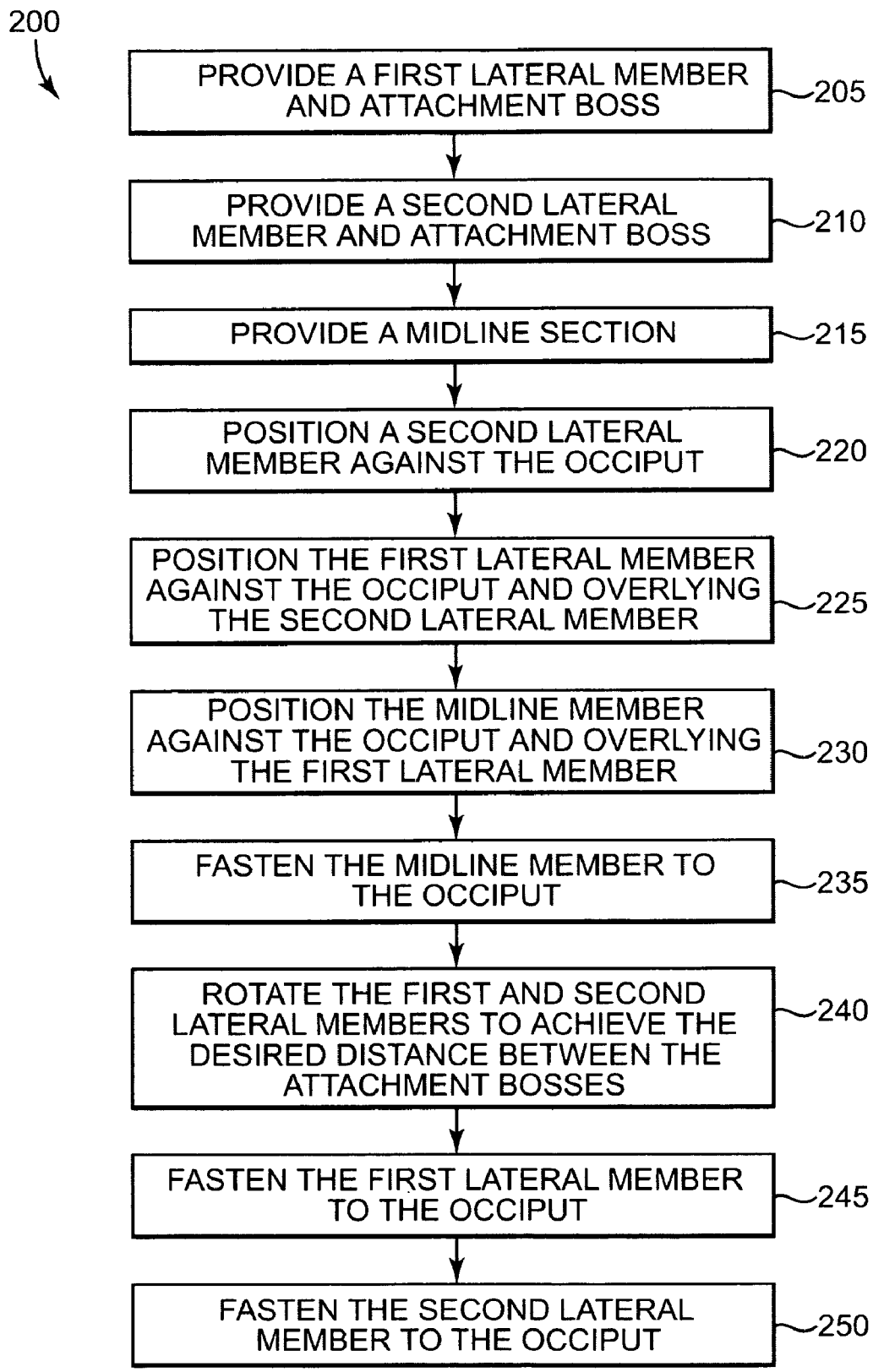
FIG. 6 shows an exemplary method of using the variable geometry occipital fixation device of FIG. 1.

FIG. 6 shows an exemplary method 200 of using the occipital fixation bracket 10 of the present invention. A first lateral member 12 and a first attachment boss 34 are provided (block 205). Then, a second lateral member 14 and a second attachment boss 34 are provided (block 210). The attachment bosses 34 are preferably inserted into the first and second lateral members 12 and 14 prior to surgery. A midline section 16 is also provided (block 215).

The second lateral member 14 is positioned in the desired location against the occiput (block 220). The first lateral member 12 is positioned against the occiput and overlying the second lateral member 14 so that the pivot bores 36 and 44 rotate around a common axis 60 (block 225). The midline member 16 is then positioned against the occiput and overlying the first lateral member 12 (block 230). The pivot bore 52 is aligned with the pivot bores 36 and 44.

Next, fasteners are inserted through the pivot bore 52 and the fixation bore 54 of the midline member 16 and into the occiput, thereby attaching the midline member 16 to the occiput (block 235). The first lateral member 12 and the second lateral member 14 are rotated around the common axis 60 until the desired distance 80 between the attachment bosses 34 is achieved (block 240). The attachment bosses 34 are free to rotate in their bores 22 and 28. The fasteners are then inserted into the fixation bores 38 and 46 of the first and second lateral members 12 and 14, thereby fastening them to the occiput and fixing the position of the attachment bosses 34 (blocks 245 and 250). In this manner, the variable geometry occipital fixation device may be installed and adjusted to accommodate a variety of patient sizes and anatomy.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

What is claimed is:

1. An occipital fixation method, comprising:
    positioning a second lateral member of a variable geometry occipital fixation device in a location against an occiput, wherein said second lateral member comprises a proximal end, a distal end, a pivot bore located at said proximal end, and an attachment bore located at said distal end;
    positioning a first lateral member of said variable geometry occipital fixation device against said occiput and overlying said second lateral member, wherein said first lateral member comprises a proximal end, a distal end, a pivot bore located at said proximal end, and an attachment bore located at said distal end;

positioning a midline member of said variable geometry occipital fixation device against said occiput and overlying said first lateral member, wherein said midline member comprises a proximal end, a distal end, a pivot bore located at said proximal end, and a fixation bore located at said distal end;

aligning said pivot bore of said midline member, said pivot bore of said first lateral member, and said pivot bore of said second lateral member along a common axis extending therethrough;

rotating said first lateral member, said second lateral member, or both around said common axis; and securing said variable geometry occipital fixation device to said occiput.

2. The occipital fixation method of claim 1, further comprising:

bending said first lateral member, said second lateral member, said midline member, or a combination thereof.

3. The occipital fixation method of claim 1, further comprising:

inserting attachment bosses in attachment bores of said first and second lateral members.

4. The occipital fixation method of claim 3, further comprising:

rotating said attachment bosses in said attachment bores.

5. The occipital fixation method of claim 4, further comprising:

attaching rods to said attachment bosses.

6. The occipital fixation method of claim 1, further comprising:

inserting a first fastener through said pivot bore of said midline member, said pivot bore of said first lateral member, and said pivot bore of said second lateral member;

inserting a second fastener through said fixation bore of said midline member; and fastening said first fastener and said second fastener to attach said midline member to said occiput prior to rotating said first lateral member, said second lateral member, or both around said common axis.

7. The occipital fixation method of claim 6, wherein securing said variable geometry occipital fixation device to said occiput further comprises:

inserting fasteners into fixation bores of said first and second lateral members; and fastening said fasteners to attach said first and second lateral members to said occiput.

\* \* \* \* \*